United States Patent
Kamenoue et al.

(10) Patent No.: US 11,725,143 B2
(45) Date of Patent: *Aug. 15, 2023

(54) RUST INHIBITOR, RUST INHIBITOR COMPOSITION, COATING FORMATION MATERIAL, COATING, AND METAL COMPONENT

(71) Applicant: KAO CORPORATION, Tokyo (JP)

(72) Inventors: Shogo Kamenoue, Wakayama (JP); Jun Naganuma, Sakai (JP); Hiroya Shiba, Sakai (JP); Takashi Mizooku, Tokyo (JP); Ryuya Arata, Wakayama (JP); Akiyoshi Kimura, Wakayama (JP); Hiroshi Hori, Wakayama (JP); Takashi Wakasa, Wakayama (JP); Shunsuke Koriki, Wakayama (JP)

(73) Assignee: KAO CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/605,729

(22) PCT Filed: May 28, 2020

(86) PCT No.: PCT/JP2020/021208
§ 371 (c)(1),
(2) Date: Oct. 22, 2021

(87) PCT Pub. No.: WO2020/241784
PCT Pub. Date: Dec. 3, 2020

(65) Prior Publication Data
US 2022/0213383 A1    Jul. 7, 2022

(30) Foreign Application Priority Data

May 28, 2019  (JP) ................................ 2019-099445
May 28, 2019  (JP) ................................ 2019-099462
Mar. 11, 2020 (JP) ................................ 2020-042161

(51) Int. Cl.
*C09K 15/06*        (2006.01)
*C07C 43/13*        (2006.01)
(Continued)

(52) U.S. Cl.
CPC ............ *C09K 15/06* (2013.01); *C07C 43/132* (2013.01); *C09D 5/086* (2013.01); *C10M 129/16* (2013.01);
(Continued)

(58) Field of Classification Search
CPC ...... C09K 15/06; C07C 43/132; C09D 5/086; C10M 129/16; C10M 169/04;
(Continued)

(56) References Cited

U.S. PATENT DOCUMENTS 3,639,240 A * 2/1972 Mutchler .............. C07C 323/00
                                                      252/396
4,719,084 A   1/1988 Schmid et al.
(Continued)

FOREIGN PATENT DOCUMENTS

CN       1826400 A   8/2006
CN    101412566 A   4/2009
(Continued)

OTHER PUBLICATIONS

"Synthesis and Application of Aliphatic Glycidyl Ethers," China Academic Journal Electronic Publishing House, 1995, pp. 15-21.
(Continued)

*Primary Examiner* — Ellen M McAvoy
(74) *Attorney, Agent, or Firm* — Birch, Stewart, Kolasch & Birch, LLP

(57) ABSTRACT

The present invention provides: a rust inhibitor that has excellent rust inhibiting and anti-corrosive properties, not only on iron members, but also on non-iron metal members,
(Continued)

and can prevent rust and corrosion over long periods; a rust inhibitor composition that contains the rust inhibitor, a coating formation material; a coating obtained from the rust inhibitor, the rust inhibitor composition, or the coating formation material; and a metal component that comprises the coating. This rust inhibitor contains at least one compound represented by a Chemical Formula (1).

[Chemical Formula (1)]

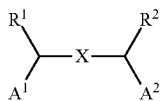

(In the formula: $R^1$ is a hydrogen atom or an aliphatic hydrocarbon group with a carbon number of 1-33; $R^2$ is an aliphatic hydrocarbon group with a carbon number of 1-33; the total carbon number of $R^1$ and $R^2$ is 1-34; X is a single bond or an aliphatic hydrocarbon group with a carbon number of 1-5; either $A^1$ or $A^2$ is —OH; and the other is —O—$CH_2$—CH(OH)—$CH_2$OH or —O—CH(—$CH_2$—OH$)_2$.)

20 Claims, 1 Drawing Sheet

(51) Int. Cl.
| | | |
|---|---|---|
| C09D 5/08 | (2006.01) | |
| C10M 129/16 | (2006.01) | |
| C10M 169/04 | (2006.01) | |
| C11D 3/00 | (2006.01) | |
| C11D 3/20 | (2006.01) | |
| C23F 11/00 | (2006.01) | |
| C10N 30/12 | (2006.01) | |
| C10N 40/22 | (2006.01) | |

(52) U.S. Cl.
CPC ......... *C10M 169/04* (2013.01); *C11D 3/0073* (2013.01); *C11D 3/2068* (2013.01); *C23F 11/00* (2013.01); *C10M 2203/003* (2013.01); *C10M 2207/04* (2013.01); *C10N 2030/12* (2013.01); *C10N 2040/22* (2013.01)

(58) Field of Classification Search
CPC ......... C10M 2203/003; C10M 2207/04; C11D 3/0073; C11D 3/2068; C23F 11/00; C10N 2030/12
USPC ......................................................... 252/396
See application file for complete search history.

(56) References Cited

U.S. PATENT DOCUMENTS

| | | | |
|---|---|---|---|
| 5,429,820 A | 7/1995 | Kamitani et al. | |
| 5,614,268 A | 3/1997 | Varley et al. | |
| 6,387,867 B1* | 5/2002 | Ishikawa | C11D 3/2068 |
| | | | 510/421 |
| 9,296,942 B2 | 3/2016 | Weerasooriya et al. | |
| 10,045,529 B2* | 8/2018 | Griese | C08G 65/2609 |
| 2001/0012821 A1* | 8/2001 | Koishikawa | C10M 129/54 |
| | | | 508/579 |
| 2002/0025295 A1 | 2/2002 | Kim | |
| 2004/0266647 A1* | 12/2004 | Kubo | C11D 3/2068 |
| | | | 510/421 |
| 2005/0037931 A1 | 2/2005 | Rowland et al. | |
| 2007/0155635 A1 | 7/2007 | Tagawa et al. | |
| 2010/0222603 A1* | 9/2010 | Selifonov | A01N 25/30 |
| | | | 549/453 |
| 2010/0274039 A1 | 10/2010 | Choi et al. | |
| 2014/0298577 A1* | 10/2014 | Burt | C11D 3/2068 |
| | | | 4/231 |
| 2015/0005225 A1 | 1/2015 | Tulchinsky et al. | |
| 2015/0133353 A1 | 5/2015 | Arai et al. | |
| 2015/0191672 A1 | 7/2015 | Hanyuda et al. | |
| 2016/0100574 A1* | 4/2016 | Pesaro | A61Q 11/00 |
| | | | 424/59 |
| 2018/0371362 A1 | 12/2018 | Keuleers et al. | |

FOREIGN PATENT DOCUMENTS

| | | |
|---|---|---|
| CN | 101909744 A | 12/2010 |
| CN | 104350137 A | 2/2015 |
| CN | 107313271 A | 11/2017 |
| JP | 53-137905 A | 12/1978 |
| JP | 55-105632 A | 8/1980 |
| JP | 62-235487 A | 10/1987 |
| JP | 5-984 A | 1/1993 |
| JP | 2002-235093 A | 8/2002 |
| JP | 2007-146029 A | 6/2007 |
| JP | 2008-506810 A | 3/2008 |
| JP | 2010-260917 A | 11/2010 |
| JP | 2012-506895 A | 3/2012 |
| JP | 2014-25040 A | 2/2014 |
| JP | 2015-501363 A | 1/2015 |
| JP | 2015-124392 A | 7/2015 |
| JP | 2016-56111 A | 4/2016 |
| JP | 2016-148095 A | 8/2016 |
| JP | 2017-197732 A | 11/2017 |
| JP | 2018-104752 A | 7/2018 |
| JP | 2018-172620 A | 11/2018 |
| JP | 2019-6998 A | 1/2019 |
| KR | 2001-0111811 A | 12/2001 |
| WO | WO 00/43479 A1 | 7/2000 |
| WO | WO 2005/018300 A2 | 3/2005 |
| WO | WO 2007/062112 A2 | 5/2007 |
| WO | WO 2010/049465 A1 | 5/2010 |
| WO | WO 2013/062679 A1 | 5/2013 |
| WO | WO 2017/090193 A1 | 6/2017 |

OTHER PUBLICATIONS

English translation of the Chinese Search Report for Chinese Application No. 202080030437.3, dated May 31, 2022.
Extended European Search Report for European Application No. 20812820.7, dated Jul. 1, 2022.
Extended European Search Report for European Application No. 20813026.0, dated Jul. 1, 2022.
Extended European Search Report for European Application No. 20813622.6, dated Jul. 1, 2022.
Extended European Search Report for European Application No. 20814785.0, dated Jun. 24, 2022.
International Preliminary Report on Patentability and English translation of the Written Opinion of the International Searching Authority for International Application No. PCT/JP2020/021174, dated Dec. 9, 2021.
International Preliminary Report on Patentability and English translation of the Written Opinion of the International Searching Authority for International Application No. PCT/JP2020/021194, dated Dec. 9, 2021.
International Preliminary Report on Patentability and English translation of the Written Opinion of the International Searching Authority for International Application No. PCT/JP2020/021208, dated Dec. 9, 2021.
International Preliminary Report on Patentability and English translation of the Written Opinion of the International Searching Authority for International Application No. PCT/JP2020/021211, dated Dec. 9, 2021.
International Preliminary Report on Patentability and English translation of the Written Opinion of the International Searching Authority for International Application No. PCT/JP2020/021213, dated Dec. 9, 2021.

(56) References Cited

OTHER PUBLICATIONS

English translation of the Chinese Search Report for Chinese Application No. 202080032131.1, dated Aug. 23, 2022.
Lai et al., "Surfactants and Detergents," Advances in Fine Petrochemicals, vol. 11, No. 3, 1997, 53 pages total, with an English translation.
U.S. Appl. No. 17/604,816, filed Oct. 19, 2021.
U.S. Appl. No. 17/605,740, filed Oct. 22, 2021.
U.S. Appl. No. 17/605,705, filed Oct. 22, 2021.
U.S. Appl. No. 17/605,921, filed Oct. 22, 2021.
International Search Report for International Application No. PCT/JP2020/021174, dated Aug. 11, 2020.
International Search Report for International Application No. PCT/JP2020/021194, dated Aug. 18, 2020.
International Search Report for International Application No. PCT/JP2020/021208, dated Aug. 25, 2020.
International Search Report for International Application No. PCT/JP2020/021211, dated Aug. 18, 2020.
International Search Report for International Application No. PCT/JP2020/021213, dated Jul. 21, 2020.

\* cited by examiner

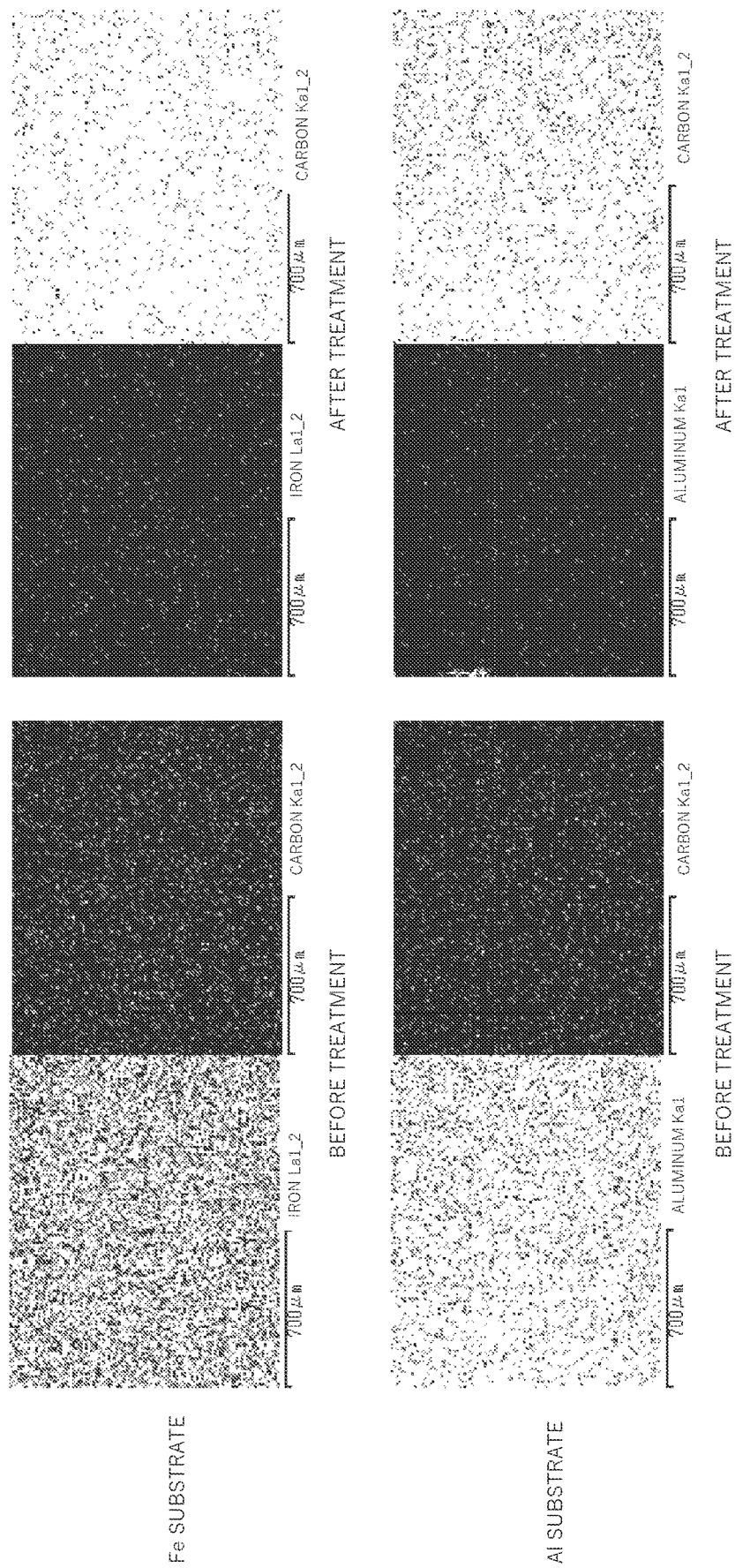

RUST INHIBITOR, RUST INHIBITOR COMPOSITION, COATING FORMATION MATERIAL, COATING, AND METAL COMPONENT

TECHNICAL FIELD

The present invention relates to a rust inhibitor, a rust inhibitor composition containing the rust inhibitor, a coating formation material, a coating obtained from the rust inhibitor, the rust inhibitor composition, or the coating formation material, and a metal component having the coating.

BACKGROUND ART

On the surface of a metal member (for example, members of iron such as steel and cast iron; members of non-ferrous metal such as copper, sine, aluminum, and alloys of these metals), rust such as an oxide, a hydroxide, or a salt such as carbonate is easily generated due to moisture, oxygen, carbon dioxide, and the like in the atmosphere. In addition, corrosion proceeds from the surface to the inside, so that the metal member is easily chemically deteriorated.

In order to prevent generation of such rust, a rust inhibitor is used. Examples of the rust inhibitor are known including organic rust inhibitors such as organic amine salts, carboxylic acid-based compounds, carboxylate salt-based compounds, sulfonate salt-based compounds, and heterocyclic compounds; and phosphorus rust inhibitors such as phosphate salt and phosphate ester.

For example, Patent Document 1 discloses an aqueous rust inhibitor composition obtained by blending a carboxylic acid having a specific polyoxyethylene structure with an aromatic carboxylic acid.

Patent Document 2 discloses a detergent, composition for a steel plate containing an alkaline agent, a chelating agent, a surfactant, a specific amine compound, and water (component E).

Patent Document 3 discloses a rust inhibitor composition containing a vaporizable rust inhibitor, phospholipid, and a solvent.

PRIOR ART DOCUMENTS

Patent Document

Patent Document 1: JP-A-2016-148095
Patent Document 2: JP-A-2018-104752
Patent Document 3: JP-A-2015-124392

SUMMARY OF THE INVENTION

Problems to be Solved by the Invention

In recent years, for the purpose of weight reduction and the like, metal components in which an iron member and a non-ferrous metal member are combined are often used, and a practical rust inhibitor having high rust prevention/corrosion prevention performance and capable of preventing rust and corrosion over a long period of time is required for the combined metal components.

The present invention has been made in view of the above circumstances, and provides a rust inhibitor which has excellent rust prevention/corrosion prevention performance not only for iron members but also for non-ferrous metal members, and can prevent rust and corrosion over a long period of time, a rust inhibitor composition containing the rust inhibitor, a coating formation material, a coating obtained from the rust inhibitor, the rust inhibitor composition, or the coating formation material, and a metal component having the coating.

Means for Solving the Problems

As a result of intensive studies, the present inventor has found that the above problem can be solved by the following rust inhibitor or the like.

The present invention relates to a rust inhibitor comprising at least one kind of a compound represented by a Chemical Formula (1):

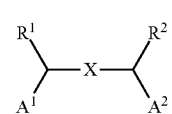

[Chemical Formula (1)]

wherein $R^1$ is a hydrogen atom or an aliphatic hydrocarbon group having 1 or more and 33 or less carbon atoms, $R^2$ is an aliphatic hydrocarbon group having 1 or more and 33 or less carbon atoms, a total number of carbon atoms of $R^1$ and $R^2$ is 1 or more and 34 or less, X is a single bond or an aliphatic hydrocarbon group having 1 or more and 5 or less carbon atoms, and one of $A^1$ and $A^2$ is —OH and the other is —O—$CH_2$—CH(OH)—$CH_2$OH or —O—CH(—$CH_2$—OH$)_2$.

Also, the present invention relates to a coating formation material comprising at least one kind of a compound represented by a Chemical Formula (1):

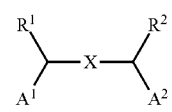

[Chemical Formula (1)]

wherein $R^1$ is a hydrocarbon atom or an aliphatic hydrocarbon group having 1 or more and 33 or less carbon atoms, $R^2$ is an aliphatic hydrocarbon group having 1 or more and 33 or less carbon atoms, a total number of carbon atoms of $R^1$ and $R^2$ is 1 or more and 34 or less, X is a single bond or an aliphatic hydrocarbon group having 1 or more and 5 or less carbon atoms, and one of $A^1$ and $A^2$ is —OH and the other is —O—$CH_2$—CH(OH)—$CH_2$OH or —O—CH(—$CH_2$—OH$)_2$.

Effect of the Invention

The present invention provides a rust inhibitor, a rust inhibitor composition containing the rust inhibitor, a coating formation material, a coating obtained from the rust inhibitor, the rust inhibitor composition, or the coating formation material, and a metal component having the coating.

The rust inhibitor of the present invention has excellent rust prevention/corrosion prevention performance, and can prevent rust and corrosion over a long period of time. In addition, since the rust inhibitor of the present invention has excellent rust prevention/corrosion prevention performance not only for iron members but also for non-ferrous metal members, the rust inhibitor can prevent rust and corrosion over a long period of time even for metal components in which an iron member and a non-ferrous metal member are combined.

It is considered that the conventional rust inhibitor is easily detached from the surface of metal components, so that dew condensation is adsorbed on the surface of the metal components from which the rust inhibitor has been detached to cause rust and corrosion. On the other hand, it is considered that since the rust inhibitor of the present invention has a glyceryl ether group and a hydroxyl group, the rust inhibitor is firmly bonded to the surface of metal components to form a coating which is hardly detached from the surface of the metal components. In addition, since it is considered that the rust inhibitor of the present invention has an aliphatic hydrocarbon group at the molecular terminal, the rust inhibitor is excellent in the effect of eliminating water molecules, and can suppress adhesion of dew condensation to the surface of metal components. As a result, it is considered that the rust inhibitor of the present invention has excellent rust prevention/corrosion prevention performance, and can prevent rust and corrosion over a long period of time. The mechanism by which the effect of the present invention can be obtained is only a presumed mechanism, and is not limited to the presumed mechanism.

BRIEF DESCRIPTION OF THE DRAWINGS

The FIGURE shows element mapping before and after treating an Fe substrate or an Al substrate using a rust inhibitor composition prepared in Example 1-2.

MODE FOR CARRYING OUT THE INVENTION

Hereinafter, a detailed described is made of the present invention.

Rust Inhibitor

The rust inhibitor of the present invention contains at least one kind of a compound represented by the following Chemical Formula (1). In addition, the rust inhibitor of the present invention may be composed of a compound represented by the following Chemical Formula (1). In addition, the rust inhibitor of the present invention may be composed of one or more kinds of a compound represented by the following Chemical Formula (1).

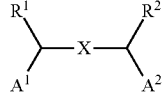

[Chemical Formula (1)]

(In Chemical Formula (1), $R^1$ is a hydrogen atom or an aliphatic hydrocarbon group having 1 or more and 33 or less carbon atoms, $R^2$ is an aliphatic hydrocarbon group having 1 or more and 33 or less carbon atoms, a total number of carbon atoms of $R^1$ and $R^2$ is 1 or more and 34 or less, X is a single bond or an aliphatic hydrocarbon group having 1 or more and 5 or less carbon atoms, and one of $A^1$ and $A^2$ is —OH and the other is —O—$CH_2$—CH(OH)—$CH_2OH$ or —O—CH(—$CH_2$—OH)$_2$.

$R^1$ is a hydrogen atom or an aliphatic hydrocarbon group having 1 or more and 33 or less carbon atoms, or from the viewpoint of having excellent rust prevention/corrosion prevention performance not only for iron members but also for non-ferrous metal members, and from the viewpoint of stability when blended in the rust inhibitor composition, preferably an aliphatic hydrocarbon group having 1 or more and 33 or less carbon atoms. $R^2$ is an aliphatic hydrocarbon group having 1 or more and 33 or less carbon atoms. Each of the aliphatic hydrocarbon groups of $R^1$ and $R^2$ is preferably a linear alkyl group or a branched alkyl group (also referred to as a branched chain alkyl group), more preferably a linear alkyl group. Each of the aliphatic hydrocarbon groups of $R^1$ and $R^2$ may have a substituent such as a halogen group, a hydroxy group, a ketone group, a carboxyl group, an aryl group, or an alkoxy group as long as the effect of the present invention is not impaired. $R^1$ and $R^2$ may be the same aliphatic hydrocarbon groups as each other or different aliphatic hydrocarbon groups from each other. In addition, the total number of substituents of $R^1$ and $R^2$ is preferably 5 or less, more preferably 3 or less, further preferably 1 or less, still more preferably 0 (that is, having no substituent) from the viewpoint of solubility in solvent.

The total number of carbon atoms of $R^1$ and $R^2$ is 1 or more and 34 or less, or from the viewpoint of having excellent rust prevention/corrosion prevention performance not only for iron members but also for non-ferrous metal members, preferably 12 or more, more preferably 14 or more, further preferably 16 or more, still more preferably 18 or more, and preferably 30 or leas, more preferably 20 or less from the viewpoint of solubility in solvent.

X is a single bond or an aliphatic hydrocarbon group having 1 or more and 5 or less carbon atoms, or from the viewpoint of having excellent rust prevention/corrosion prevention performance not only for iron members but also for non-ferrous metal members, preferably a single bond or an aliphatic hydrocarbon group having 1 or more and 3 or less carbon atoms, more preferably a single bond or an aliphatic hydrocarbon group having 1 or more and 2 or less carbon atoms, further preferably a single bond or an aliphatic hydrocarbon group having 1 carbon atom, still more preferably a single bond.

The total number of carbon atoms of $R^1$, $R^2$ and X is 1 or more and 39 or less, or from the viewpoint of having excellent rust prevention/corrosion prevention performance not only for iron members but also for non-ferrous metal members, preferably 12 or more, more preferably 34 or more, further preferably 16 or more, still more preferably 18 or more, and preferably 30 or less, more preferably 28 or less, further preferably 26 or less, still more preferably 25 or less, still more preferably 24 or less, still more preferably 22 or less, still more preferably 20 or less.

When X is the aliphatic hydrocarbon group, X is preferably a linear alkyl group or branched alkyl group, more preferably a linear alkyl group from the viewpoint of having excellent rust prevention/corrosion prevention performance not only for iron members but also for non-ferrous metal members, and production efficiency and ease of production.

From the viewpoint of having excellent rust prevention/corrosion prevention performance not only for iron members but also for non-ferrous metal members, and production efficiency and ease of production, X is preferably

*—($CH_2$)$_n$—* (n is 0 or more and 5 or less, and * represents a binding site), wherein n is preferably 0 or more, preferably 3 or less, more preferably 2 or less, further preferably 1 or less, still more preferably 0, that is, a single bond.

From the viewpoint of having excellent rust prevention/corrosion prevention performance not only for iron members but also for non-ferrous metal members, and production efficiency and ease of production, the rust inhibitor preferably contains two or more kinds of the compound, between which the total numbers of carbon atoms of $R^1$ and $R^2$ are the same, but the numbers of carbon atoms of $R^1$ and the numbers of carbon atoms of $R^2$ are each different.

From the viewpoint of having excellent rust prevention/corrosion prevention performance not only for iron members but also for non-ferrous metal members, and production efficiency and ease of production, the rust inhibitor preferably contains two or more kinds of the compound, between which the total numbers of carbon atoms of $R^1$, $R^2$ and X are the same, but the numbers of carbon atoms of $R^1$ and the numbers of carbon atoms of $R^2$ are each different.

From the viewpoint of having excellent rust prevention/corrosion prevention performance not only for iron members but also for non-ferrous metal members, and production efficiency and ease of production, the rust inhibitor preferably contains two or more kinds of the compound in which X is a single bond or an aliphatic hydrocarbon group having 1 or more and 3 or less carbon atoms, and between which the total numbers of carbon atoms of $R^1$ and $R^2$ are the same, but the numbers of carbon atoms of $R^1$ and the numbers of carbon atoms of $R^2$ are each different.

From the viewpoint of having excellent rust prevention/corrosion prevention performance not only for iron members but also for non-ferrous metal members, and production efficiency and ease of production, the rust inhibitor preferably contains two or more kinds of the compound in which X is a single bond or an aliphatic hydrocarbon group having 1 or more and 3 or less carbon atoms, and between which the total numbers of carbon atoms of $R^1$, $R^2$ and X are the same, but the numbers of carbon atoms of $R^1$ and the numbers of carbon atoms of $R^2$ are each different.

From the viewpoint of having excellent rust prevention/corrosion prevention performance not only for iron members but also for non-ferrous metal members, and production efficiency and ease of production, the rust inhibitor preferably contains two or more hinds of the compound in which X is a single bond or an aliphatic hydrocarbon group having 1 or more and 2 or less carbon atoms, and between which the total numbers of carbon atoms of $R^1$ and $R^2$ are the same, but the numbers of carbon atoms of $R^1$ and the numbers of carbon atoms of $R^2$ are each different.

From the viewpoint of having excellent rust prevention/corrosion prevention performance not only for iron members but also for non-ferrous metal members, and production efficiency and ease of production, the rust inhibitor preferably contains two or more kinds of the compound in which X is a single bond or an aliphatic hydrocarbon group having 1 or more and 2 or less carbon atoms, and between which the total numbers of carbon atoms of $R^1$, $R^2$ and X are the same, but the numbers of carbon atoms of $R^1$ and the numbers of carbon atoms of $R^2$ are each different.

From the viewpoint of having excellent rust prevention/corrosion prevention performance not only for iron members but also for non-ferrous metal members, and production efficiency and ease of production, the rust inhibitor preferably contains two or more kinds of the compound in which X is a single bond or an aliphatic hydrocarbon group having 1 carbon atom, and between which the total numbers of carbon atoms of $R^1$ and $R^2$ are the same, but the numbers of carbon atoms of $R^1$ and the numbers of carbon atoms of $R^2$ are each different.

From the viewpoint of having excellent rust prevention/corrosion prevention performance non only for iron members but also for non-ferrous metal members, and production efficiency and ease of production, the rust inhibitor preferably contains two or more kinds of the compound in which X is a single bond or an aliphatic hydrocarbon group having 1 carbon atom, and between which the total numbers of carbon atoms of $R^1$, $R^2$ and X are the same, but the numbers of carbon atoms of $R^1$ and the numbers of carbon atoms of $R^2$ are each different.

From the viewpoint of having excellent rust prevention/corrosion prevention performance not only for iron members but also for non-ferrous metal members, and production efficiency and ease of production, the rust inhibitor preferably contains two or more kinds of the compound in which X is a single bond, and between which the total numbers of carbon atoms of $R^1$ and $R^2$ are the same, but the numbers of carbon atoms of $R^1$ and the numbers of carbon atoms of $R^2$ are each different.

When the rust inhibitor contains two or more kinds of the compound in which X is a single bond and between which the total numbers of carbon atoms of $R^1$ and $R^2$ are different, the total content of two or more kinds of the compound selected from a compound in which the total number of carbon atoms of $R^1$ and $R^2$ is 12, a compound in which the total number of carbon atoms of $R^1$ and $R^2$ is 14, and a compound in which the total number of carbon atoms of $R^1$ and $R^2$ is 16 is preferably 75 mass % or more, more preferably 85 mass % or more, further preferably 95 mass % or more, still more preferably 100 mass % from the viewpoint of having excellent rust prevention/corrosion prevention performance not only for iron members but also for non-ferrous metal members.

When the rust inhibitor contains two or more kinds of the compound in which X is a single bond and between which the total numbers of carbon atoms of $R^1$ and $R^2$ are different, the total content of a compound in which the total number of carbon atoms of $R^1$ and $R^2$ is 14, and a compound in which the total number of carbon atoms of $R^1$ and $R^2$ is 16 is preferably 75 mass %, or more, more preferably 85 mass % or mere, further preferably 95 mass % or more, still more preferably 99 mass % or more, still mere preferably 100 mass % from the viewpoint of having excellent rust prevention/corrosion prevention performance not only for iron members but also for non-ferrous metal members.

When the rust inhibitor contains two or more kinds of the compound represented by the Chemical Formula (1) between which the total numbers of carbon atoms of $R^1$ and $R^2$ are the same, but the numbers of carbon atoms of $R^1$ and the numbers of carbon atoms of $R^2$ are each different, the content ratio of the compound in which the number of carbon atoms of $R^1$ is 5 or more and the number of carbon atoms of $R^2$ is 5 or more is preferably 10 mass % or more, more preferably 20 mass % or more, further preferably 30 mass % or more, and preferably 90 mass % or less, more preferably 80 mass % or less, further preferably 70 mass % or less from the viewpoint of having excellent rust prevention/corrosion prevention performance not only for iron members but also for non-ferrous metal members, and production efficiency and ease of production.

The method for producing the compound represented by the Chemical Formula (1) is not particularly limited. For example, the compound can be produced by oxidizing the double bond in an internal or terminal olefin with a peroxide such as hydrogen peroxide, performic acid, or peracetic acid to synthesize an internal or terminal epoxide, and reacting the obtained internal or terminal epoxide with glycerin. In the case of a mixture in which the total numbers of carbon atoms of internal or terminal olefins are constant but the double bonds are present at different positions, the compound represented by the Chemical Formula (1) obtained by the above producing method is a mixture of a plurality of compounds in which X is a single bond and between which the total numbers of carbon atoms of $R^1$ and $R^2$ are the same, but the numbers of carbon atoms of $R^1$ and the numbers of carbon atoms of $R^2$ are each different. The compound represented by the Chemical Formula (1) obtained by the above producing method is usually a mixture of a compound 1 in which one of $A^1$ and $A^2$ is —OH and the other is —O—$CH_2$—CH(OH)—$CH_2$OH (hereinafter, also referred to as ether alcohol 1) and a compound 2 in which one of $A^1$ and $A^2$ is —OH and the other is —O—CH(—$CH_2$—OH)$_2$ (hereinafter, also referred to as ether alcohol 2).

The internal olefin used for the production of the compound represented by the Chemical Formula (1) may contain a terminal olefin. In this case, the content of terminal olefin contained in olefin is, for example, 0.1 mass % or more, 0.2 mass % or more, and 5 mass % or less, 3 mass % or less, 2 mass % or less, 1 mass % or less, 0.5 mass % or less.

When the rust inhibitor contains the ether alcohol 1 and the ether alcohol 2, the content of the ether alcohol 1 is preferably 1 mass % or more, more preferably 30 mass % or more, further preferably 40 mass % or more, still more preferably 50 mass % or more, end preferably 99 mass % or less, more preferably 90 mass % or less, further preferably 80 mass % or less with respect, to the total amount of the ether alcohol 1 and the ether, alcohol 2, from the viewpoint of having excellent rust prevention/corrosion prevention performance not only for iron members but also for non-ferrous metal members. From the same viewpoint, the content is preferably 1 to 99 mass %, more preferably 30 to 99 mass %, further preferably 40 to 90 mass %, still more preferably 50 to 80 mass %.

The rust inhibitor, can be obtained as one hind of the compound represented by the Chemical Formula (1), a mixture of two or more kinds of the compound represented by the Chemical Formula (1), or a mixture of the above compound and a trace component other than olefin contained in the raw material olefin and a derivative thereof.

The rust inhibitor is used, for example, as a raw material for a cutting oil, a rust preventive oil, or a detergent. In addition, the rust inhibitor is used as a forming material for a coating with which the surface of various metal components is coated. Since the rust inhibitor has excellent rust prevention/corrosion prevention performance not only for iron members but also for non-ferrous metal members, the rust inhibitor is preferably used as a forming material for a coating with which the surface of metal components in which an iron member and a non-ferrous metal member are combined is coated.

Rust Inhibitor Composition

The rust inhibitor composition of the present invention contains at least the rust inhibitor.

The content of the rust inhibitor in the rust inhibitor composition is not particularly limited, but is preferably 0.01 mass % or more, more preferably 0.1 mass % or more, further preferably 1 mass % or more from the viewpoint of having excellent rust prevention/corrosion prevention performance not only for iron members but also for non-ferrous metal members, or is preferably 15 mass % or less, more preferably 10 mass % or less, further preferably 5 mass % or less from the viewpoint of reducing the added amount of a solubilizing agent or the like.

The rust inhibitor composition of the present invention can contain water. The content of water in the rust inhibitor composition is preferably 10% or more, more preferably 30% or more, further preferably 50% or more from the viewpoint of ease of application and the like, and preferably 99.9999% or less, more preferably 99.999% or less, further preferably 99.99% or less from the viewpoint of rust prevention/corrosion prevention performance. In addition, the content of water in the rust inhibitor composition may be the balance exclusive of the contents of the rust inhibitor and the other components (other than the rust inhibitor and water). Examples of the water include ion-exchanged water, distilled water, RO water, and tap water.

The rust inhibitor, composition may contain a solubilizing agent for dissolving the rust inhibitor. Examples of the solubilizing agent include methanol, ethanol, propyl alcohol, butyl alcohol, ethylene glycol, propylene glycol, diethylene glycol, dipropylene glycol, diethylene glycol monomethyl ether, diethylene glycol monoethyl ether, diethylene glycol monobutyl ether, diethylene glycol monobutyl ether acetate, glycerin, trimethylolethane, trimethylolpropane, neopehtyl glycol, 1,6-hexanediol, 1,2,6-hexanetriol, pentaerythritol, and sorbitol. These may be used alone or in combination of two or more kinds thereof.

The content of the solubilizing agent in the rust inhibitor composition is not particularly limited, but is preferably 3 mass % or more, more preferably 5 mass % or more, further preferably 10 mass % or more from the viewpoint of dissolving the rust inhibitor, and is preferably 80 mass % or less, more preferably 50 mass % or less, further preferably 30 mass % or less, still more preferably 20 mass % or less from the viewpoint of having excellent rust prevention/corrosion prevention performance not only for iron members but also for non-ferrous metal members.

In addition, the rust inhibitor composition may contain an acid component and/or an alkali component from the viewpoint of having excellent rust prevention/corrosion prevention, performance not only for iron members but also for non-ferrous metal members, and from the viewpoint of dissolving the rust inhibitor. The acid component and the alkali component may partially form a salt to exist in the rust inhibitor composition, or may all form a salt.

The acid component is not particularly limited, and examples thereof include aliphatic carboxylic acids such as acetic acid, propionic acid, butanoic acid, pentanoic acid, hexanoic acid, heptanoic acid, octanoic acid, nonanoic acid, decanoic acid, undecanoic acid, dodecanoic acid, tridecanoic acid, tetradecanoic acid, pentadecanoic acid, hexadecanoic acid, heptadecanoic acid, octadecanoic acid, propanedioic acid, butanedioic acid, pentanedioic acid, hexanedioic acid, heptandioic acid, octanedioic acid, nonanedioic acid, decanedioic acid, undecanedioic acid, dodecanedioic acid, tridecanedioic acid, tatradecanadioic acid, pentadecanedioic acid, hexadecanedioic acid, heptadecanedioic acid, octadecanedioic acid, nonadocanodioic acid, citric acid, glycolic acid, lactic acid, acrylic acid, methacrylic acid, crotonic acid, oleic acid, fumaric acid, and maleic acid; and aromatic carboxylic acids such as benzoic acid, p-toluic acid, p-ethylbenzoic acid, p-isopropylbenoic acid, p-tert-butylbenzoic acid, xylylic acid, isophthalic acid, terephthalic acid, salicylic acid, cinnamic acid, toluic acid, hemimellitic acid, trimellitic acid, trimesic acid, hydroxybenzoic acid, dihydroxybenzoic acid, and trihydrobenzoic acid. These may be used alone or in combination of two or more kinds thereof. The acid component is preferably an aliphatic carboxylic acid, more preferably an aliphatic carboxylic acid having 4 to 12 carbon atoms, further preferably an aliphatic carboxylic acid having 6 to 8 carbon atoms.

The content of the acid component in the rust inhibitor composition is not particularly limited, but is preferably 0.5 mass % or more, more preferably 1 mass % or more, further preferably 2 mass % or more from the viewpoint of having excellent rust prevention/corrosion prevention performance not only for iron members but also for non-ferrous metal members and from the viewpoint of dissolving the rust inhibitor, and is preferably 20 mass % or less, more preferably 15 mass % or less, further preferably 10 mass % or less from the viewpoint of having excellent rust prevention/corrosion prevention performance not only for iron members but also for non-ferrous metal members.

The alkali, component is not particularly limited, and examples thereof include inorganic alkalis such as sodium hydroxide, potassium hydroxide, and ammonia; and organic alkalis such as tetramethylammonium hydroxide, monoethanolamine, diethanolamine, triethanolamine, methylamine, dimethylamine, trimethylamine, ethylamine, diethylamine, triethylamine, methylethanolamine, dimethylethanolamine, methyldietylanolamine, ethylethanolamine, diethylethanolamine, ethyldiethanolamine, cyclohexylamine, and triisopanolamine. These may be used alone or in combination of two or more kinds thereof. The alkali component is preferably an organic alkali.

The content of the alkali component in the rust inhibitor composition is not particularly limited, but is preferably 0.5 mass % or more, more preferably 1 mass % or more, further preferably 2 mass % or more from the viewpoint of having excellent rust prevention/corrosion prevention performance not only for iron members but also for non-ferrous metal members and from the viewpoint of dissolving the rust inhibitor, and is preferably 20 mass % or less, more preferably 15 mass % or less, further preferably 10 mass % or less from the viewpoint of having excellent rust prevention/corrosion prevention performance not only for iron members but also for non-ferrous metal members.

The pH of the rust inhibitor composition is not particularly limited, but is preferably 3 or more, more preferably 5 or more, further preferably 7 or more, and preferably 12 or less, more preferably 10 or less, further preferably 9 or less from the viewpoint of having excellent rust prevention/corrosion prevention performance not only for iron members but also for non-ferrous metal members.

The rust inhibitor composition may contain, in addition to the rust inhibitor, a base oil such as mineral oil or synthetic oil; an oily agent such as oil and fat or ester; and an additive such as a surfactant, an extreme pressure agent, a defoamer, a preservative, an antioxidant, a coupling agent, or a pH adjuster.

The rust inhibitor composition is used as, for example, a cutting oil, a rust preventive oil, and a detergent, and contains the respective components depending on the use. That is, the rust inhibitor composition may be a cutting oil, a rust preventive oil, or a detergent, and may contain the compound represented by the Chemical Formula (1).

When the rust inhibitor composition is used as a detergent, the temperature of the rust inhibitor composition is preferably 10° C. or higher, more preferably 30° C. or higher, further preferably 40° C. or higher, and preferably 90° C. or lower, more preferably 70° C. or lower, further preferably 60° C. or lower from the viewpoint of detergency and handleability.

In addition, the rust inhibitor composition can be used as a coating formation material for forming a coating on the surface of various metal components.

When the rust inhibitor composition is used as the coating formation material, the rust inhibitor composition preferably contains water. The content of water in the rust inhibitor composition is not particularly limited, but is preferably 60 mass % or more, more preferably 90 mass % or more, further preferably 95 mass % or more, and preferably 99.9 mass % or less, more preferably 93 mass % or less, further preferably 98 mass % or less from the viewpoint of having excellent rust prevention/corrosion prevention performance not only for iron members but also for non-ferrous metal members and from the viewpoint of forming a uniform coating.

Coating Formation Material

The coating formation material of the present invention contains at least one kind of the compound represented by the Chemical Formula (1). In addition, the coating formation material of the present invention may be composed of the compound represented by the Chemical Formula (1). In addition, the coating formation material of the present invention may be composed of one or more kinds of the compound represented by the Chemical Formula (1). The description regarding the compound represented by the Chemical Formula (1) is as described above. The coating formation material of the present invention is useful as the rust inhibitor. Examples of the use of the coating formation material of the present invention include uses as a out ting oil, paint, an antifogging agent, an antifouling agent, and an anti-icing agent.

Coating

The coating of the present invention can be obtained from the rust inhibitor, the rust inhibitor composition, or the coating formation material. Examples of the method for forming the coating include a method including directly applying the rust inhibitor or the coating formation material to a metal member or the like, and a method including immersing a metal member or the like in a liquid containing the rust inhibitor composition or the coating formation material.

The thickness of the coating of the present invention is preferably 1 nm or more, more preferably 3 nm or more from the viewpoint of having rust prevention/corrosion prevent ion performance.

Examples of the use of the coating of the present invention include uses as a protective coating and a paint coating for metal components end the like such as a rust preventive coating, an antifogging coating, an antifouling coating, and an anti-icing coating.

Metal Component Having Coating

The coating of the present invention is obtained from the rust inhibitor, the rust inhibitor composition, or the coating formation material. A metal component having the coating can be produced, for example, by spraying, dropping, or applying the rust inhibitor, the rust inhibitor composition, or the coating formation material to the surface of the metal component, or immersing the metal component in the rust inhibitor, the rust inhibitor composition, or the coating formation material, and then drying the metal component as necessary.

The metal component is not particularly limited, and examples thereof include metal components made of an iron member such as steel and cast iron; metal components made of a non-ferrous metal member such as copper, zinc, aluminum, and an alloy of these metals; and metal components in which the iron member and the non-ferrous metal member are combined.

The metal component having the coating is used in, for example, an automobile industry, a machine industry, a metal industry, an electric and electronic industry, and a chemical plant.

The present invention and preferred embodiments of the present invention are described below.

1

A rust inhibitor comprising at least one kind of a compound represented by a Chemical Formula (1):

[Chemical Formula (1)]

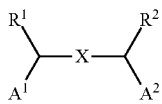

wherein $R^1$ is a hydrogen atom or an aliphatic hydrocarbon group having 1 or more and 33 or less carbon atoms, $R^2$ is an aliphatic hydrocarbon group having 1 or more and 33 or less carbon atoms, a total number of carbon atoms of $R^1$ and $R^2$ is 1 or more and 34 or less, X is a single bond or an aliphatic hydrocarbon group having 1 or more and 5 or less carbon atoms, and one of $A^1$ and $A^2$ is —OH and the other is —O—$CH_2$—CH(OH)—$CH_2$OH or —O—CH(—$CH_2$—OH)$_2$.

2

A rust inhibitor, comprising at least one kind of a compound represented by a Chemical Formula (1):

[Chemical Formula (1)]

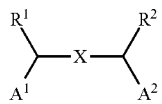

wherein $R^1$ is a hydrogen atom or an aliphatic hydrocarbon group having 1 or more and 33 or less carbon atoms, $R^2$ is an aliphatic hydrocarbon group having 1 or more and 33 or less carbon atoms, X is a single bond or an aliphatic hydrocarbon group having 1 or more and 5 or less carbon atoms, a total number of carbon atoms of $R^1$, $R^2$ and X is 1 or more and 39 or less, and one of $A^1$ and $A^2$ is —OH and the other is —O—$CH_2$—CH(OH)—$CH_2$OH or —O—CH(—$CH_2$—OH)$_2$.

3

The rust inhibitor according to <1> or <2>, wherein $R^1$ is an aliphatic hydrocarbon group having 1 or more and 33 or less carbon atoms.

4

The rust inhibitor according to any one of <1> to <3>, wherein each of the aliphatic hydrocarbon groups is preferably a linear alkyl group or a branched alkyl group, more preferably a linear alkyl group.

5

The rust inhibitor according to any one of <1> to <4>, wherein a total number of substituents of $R^1$ and $R^2$ is preferably 5 or less, more preferably 3 or less, further preferably 1 or less, still more preferably 0.

6

The rust inhibitor according to any one of <1> to <4>, wherein a total number of carbon atoms of $R^1$ and $R^2$ is preferably 12 or more, more preferably 14 or more, further preferably 16 or more, still more preferably 18 or more, and preferably 30 or less, more preferably 20 or less.

7

The rust inhibitor according to any one of <1> to <6>, wherein X is preferably a single bond or an aliphatic hydrocarbon group having 1 or more and 3 or less carbon atoms, more preferably a single bond or an aliphatic hydrocarbon group having 1 or more and 2 or less carbon atoms, further preferably a single bond or an aliphatic hydrocarbon group having 1 carbon atom, still more preferably a single bond.

8

The rust inhibitor according to any one of <1> to <5>, wherein
preferably a total number of carbon atoms of $R^1$ and $R^2$ is 12 or more and 30 or less, and X is a single bond or an aliphatic hydrocarbon group having 1 or more and 3 or less carbon atoms,
more preferably a total number of carbon atoms of $R^1$ and $R^2$ is 14 or more and 20 or less, and X is a single bond or an aliphatic hydrocarbon group having 1 or more and 2 or less carbon atoms,
further, preferably a total number of carbon atoms of $R^1$ and $R^2$ is 16 or more and 20 or less, and X is a single bond or an aliphatic hydrocarbon group having 1 carbon atom,
still more preferably a total number of carbon atoms of $R^1$ and $R^2$ is 18 or more and 20 or less, and X is a single bond.

9

The rust inhibitor according to any one of <1> to <8>, wherein a total number, of carbon atoms of $R^1$, $R^2$ and X is preferably 12 or more, more preferably 14 or more, further preferably 16 or more, still more preferably 18 or more, and preferably 30 or less, more preferably 28 or less, further preferably 26 or less, still more preferably 25 or less, still more preferably 24 or less, still more preferably 22 or less, still more preferably 20 or less.

10

The rust inhibitor according to any one of <1> to <9>, wherein when X is the aliphatic hydrocarbon group, X is preferably a linear alkyl group or branched alkyl group, more preferably a linear alkyl group.

11

The rust inhibitor according to any one of <1> to <9>, wherein X is preferably
*—$(CH_2)_n$—* (n is 0 or more and 5 or less, and * represents a binding site),
wherein n is preferably 0 or more, preferably 3 or less, more preferably 2 or less, further preferably 1 or less, still more preferably 0, that is, a single, bond.

12

The rust inhibitor according to any one of <1> to <11>, comprising two or more binds of the compound in which X is a single bond or an aliphatic hydrocarbon group having 1 or more and 3 or less carbon atoms, and between which the total numbers of carbon atoms of $R^1$ and $R^2$ are the same, but the numbers of carbon atoms of $R^1$ and the numbers of carbon atoms of $R^2$ are each different.

13

The rust inhibitor according to any one of <1> to <11>, comprising two or more binds of the compound in which X is a single bond or an aliphatic hydrocarbon group having 1 or more and 3 or less carbon atoms, and between which the total numbers of carbon atoms of $R^1$, $R^2$ and X are the same, but the numbers of carbon atoms of $R^1$ and the numbers of carbon atoms of $R^2$ are each different.

14

The rust inhibitor according to any one of <1> to <11>, comprising two or more kinds of the compound in which X is a single bond or an aliphatic hydrocarbon group having 1 or more and 2 or less carbon atoms, and between which the total numbers of carbon atoms of $R^1$ and $R^2$ are the same, but the numbers of carbon atoms of $R^1$ and the numbers of carbon atoms of $R^2$ are each different.

15

The rust inhibitor according to any one of <1> to <11>, comprising two or more kinds of the compound in which X is a single bond or an aliphatic hydrocarbon group having 1 or more and 2 or less carbon atoms, and between which the total numbers of carbon atoms of $R^1$, $R^2$ and X are the same, but the numbers of carbon atoms of $R^1$ and the numbers of carbon atoms of $R^2$ are each different.

16

The rust inhibitor according to any one of <1> to <11>, comprising two or more kinds of the compound in which X is a single bond or an aliphatic hydrocarbon group having 1 carbon atom, and between which the total numbers of carbon atoms of $R^1$ and $R^2$ are the same, but the numbers of carbon atoms of $R^1$ and the numbers of carbon atoms of $R^2$ are each different.

17

The rust inhibitor according to any one of <1> to <11>, comprising two or more kinds of the compound in which X is a single bond or an aliphatic hydrocarbon group having 1 carbon atom, and between which the total numbers of carbon atoms of $R^1$, $R^2$ and X are the same, but the numbers of carbon atoms of $R^1$ and the numbers of carbon atoms of $R^2$ are each different.

18

The rust inhibitor according to any one of <1> to <11>, comprising two or more kinds of the compound in which X is a single bond, and between which the total numbers of carbon atoms of $R^1$ and $R^2$ are the same, but the numbers of carbon atoms of $R^1$ and the numbers of carbon atoms of $R^2$ are each different.

19

The rust inhibitor, according to any one of <1> to <11>, wherein when the rust inhibitor contains two or more kinds of the compound, in which X is a single bond and between which the total numbers of carbon atoms of $R^1$ and $R^2$ are different, the total content of two or more kinds of the compound selected from a compound in which the total number of carbon atoms of $R^1$ and $R^2$ is 12, a compound, in which the total number of carbon atoms of $R^1$ and $R^2$ is 14, and a compound in which the total number of carbon atoms of $R^1$ and $R^2$ is 16 is 75 mass % or more.

20

The rust inhibitor according to any one of <1> to <12>, wherein when the rust inhibitor contains two or more kinds of the compound in which X is a single bond and between which the total numbers of carbon atoms of $R^1$ and $R^2$ are different, the total content of two or more kinds of the compound selected from a compound in which the total number of carbon atoms of $R^1$ and $R^2$ is 12, a compound in which the total number of carbon atoms of $R^1$ and $R^2$ is 14, and a compound in which the total number of carbon atoms of $R^1$ and $R^2$ is 16 is 85 mass % or more.

21

The rust inhibitor according to any one of <1> to <31>, wherein when the rust inhibitor contains two or more kinds of the compound in which X is a single bond and between which the total numbers of carbon atoms of $R^1$ and $R^2$ are different, the total content of two or more kinds of the compound selected, from a compound in which the total number of carbon atoms of $R^1$ and $R^2$ is 12, a compound in which the total number of carbon atoms of $R^1$ and $R^2$ is 14, and a compound in which the total number of carbon atoms of $R^1$ and $R^2$ is 16 is 95 mass % or more.

22

The rust inhibitor according to any one of <1> to <11>, wherein when the rust inhibitor contains two or more kinds of the compound in which X is a single bond and between which the total numbers of carbon atoms of $R^1$ and $R^2$ are different, the total content of two or more kinds of the compound selected from a compound in which the total number of carbon atoms of $R^1$ and $R^2$ is 12, a compound in which the total number of carbon atoms of $R^1$ and $R^2$ is 14, and a compound in which the total number of carbon atoms of $R^1$ and $R^2$ is 16 is 100 mass %.

23

The rust inhibitor according to any one of <1> to <11>, wherein when the rust inhibitor contains two or more kinds of the compound in which X is a single bond and between which the total numbers of carbon atoms of $R^1$ and $R^2$ are different, the total content of a compound in which the total number of carbon atoms of $R^1$ and $R^2$ is 14, and a compound in which the total number of carbon atoms of $R^1$ and $R^2$ is 16 is 75 mass % or more.

24

The rust inhibitor according to any one of <1> to <11>, wherein when the rust inhibitor contains two or more kinds of the compound in which X is a single bond and between which the total numbers of carbon atoms of $R^1$ and $R^2$ are different, the total content of a compound in which the total

15 number of carbon atoms of $R^1$ and $R^2$ is 14, and a compound in which the total number of carbon atoms of $R^1$ and $R^2$ is 16 is 85 mass % or more.

25

The rust inhibitor according to any one of <1> to <11>, wherein when the rust inhibitor contains two or more kinds of the compound in which X is a single bond and between which the total numbers of carbon atoms of $R^1$ and $R^2$ are different, the total content of a compound in which the total number of carbon atoms of $R^1$ and $R^2$ is 14, and a compound in which the total number of carbon atoms of $R^1$ and $R^2$ is 16 is 95 mass % or more.

26

The rust inhibitor according to any one of <1> to <11>, wherein when the rust inhibitor contains two or more kinds of the compound in which X is a single bond and between which the total numbers of carbon atoms of $R^1$ and $R^2$ are different, the total content of a compound in which the total number of carbon atoms of $R^1$ and $R^2$ is 14, and a compound in which the total number, of carbon atoms of $R^1$ and $R^2$ is 16 is 99 mass % or more, preferably 100 mass %.

27

The rust inhibitor according to any one of <1> to <18>, wherein when the rust inhibitor contains two or more kinds of the compound represented by the Chemical Formula (1) between which the total numbers of carbon atoms of $R^1$ and $R^2$ are the same, but the numbers of carbon atoms of $R^1$ and the numbers of carbon atoms of $R^2$ are each different, the content ratio of the compound in which the number of carbon atoms of $R^1$ is 5 or more and the number of carbon atoms of $R^2$ is 5 or more is 10 mass % or more and 90 mass % or less.

23

The rust inhibitor, according to any one of <1> to <18>, wherein when the rust inhibitor contains two or more kinds of the compound represented by the Chemical Formula (1) between which the total numbers of carbon atoms of $R^1$ and $R^2$ are the same, but the numbers of carbon atoms of $R^1$ and the numbers of carbon atoms of $R^2$ are each different, the content ratio of the compound in which the number of carbon atoms of $R^1$ is 5 or more and the number of carbon atoms of $R^2$ is 5 or more is 20 mass % or more and 80 mass % or less.

29

The rust inhibitor according to any one of <1> to <18>, wherein when the rust inhibitor contains two or more kinds of the compound represented by the Chemical Formula (1) between which the total numbers of carbon atoms of $R^1$ and $R^2$ are the same, but the numbers of carbon atoms of $R^1$ and the numbers of carbon atoms of $R^2$ are each different, the content ratio of the compound in which the number of carbon atoms of $R^1$ is 5 or more and the number of carbon atoms of $R^2$ is 5 or more is 30 mass % or more and 70 mass % or less.

30

The rust inhibitor according to any one of <1> to <29>, comprising a compound 1 in which in the Chemical Formula (1), one of $A^1$ and $A^2$ is —OH and another is —O—$CH_2$—CH(OH)—$CH_2OH$, and a compound 2 in which in the Chemical Formula (1), one of $A^1$ and $A^2$ is —OH and another is —O—CH(—$CH_2$—OH)$_2$.

31

The rust inhibitor according to <30>, wherein a content of the compound 1 is preferably 1 mass % or more, more preferably 30 mass % or more, further preferably 40 mass % or more, still more preferably 50 mass % or more, and preferably 99 mass % or less, more preferably 30 mass % or loss, further preferably 80 mass % or less with respect to a total amount of the compound 1 and the compound 2.

32

The rust inhibitor according to <30>, wherein a content of the compound 1 is preferably 1 to 93 mass %, more preferably 30 to 99 mass %, further preferably 40 to 90 mass %, still more preferably 50 to 80 mass %.

33

The rust inhibitor according to any one of <1> to <32>, using as a raw material for a cutting oil, a rust preventive oil, or a detergent.

34

The rust inhibitor according to any one of <1> to <32>, using as a forming material for a coating with which a surface of a metal component is coated.

35

The rust inhibitor according to any one of <1> to <32>, using as a forming material for a coating with which a surface of a metal component in which an iron member and a non-ferrous metal member are combined is coated.

36

A rust inhibitor composition comprising the rust inhibitor according to any one of <1> to <35>.

37

The rust inhibitor composition according to <36>, wherein a content of the rust inhibitor in the rust inhibitor composition is preferably 0.01 mass % or more, more preferably 0.1 mass % or more, further preferably 1 mass % or more, and preferably 15 mass % or less, more preferably 10 mass % or less, further preferably 5 mass % or less.

38

The rust inhibitor composition according to <36> or <37>, comprising water, wherein a content of water in the rust inhibitor composition is preferably 10% or more, more preferably 30% or more, further preferably 50% or more, and preferably 99.9999% or less, more preferably 99.999% or less, further preferably 99.99% or less.

39

The rust inhibitor composition according to <36> or <37>, comprising water, wherein a content of water in the rust inhibitor composition is a balance exclusive of the contents of the rust inhibitor and the other components (other than the rust inhibitor and water).

40

The rust inhibitor composition according to any one of <36> to <39>, further comprising a solubilizing agent.

41

The rust inhibitor composition according to <40>, wherein a content of the solubilizing agent in the rust inhibitor composition is preferably 3 mass % or more, more preferably 5 mass % or more, further preferably 10 mass % or more, and preferably 80 mass % or less, more preferably 50 mass % or less, further preferably 30 mass % or less, still more preferably 20 mass % or less.

42

The rust, inhibitor composition according to any one of <36> to <41>, further comprising an acid component and/or an alkali component.

43

The rust inhibitor composition according to <42>, wherein the acid component is preferably an aliphatic carboxylic acid, more preferably an aliphatic carboxylic acid having 4 to 12 carbon atoms, further preferably an aliphatic carboxylic acid having 6 to 3 carbon atoms.

44

The rust inhibitor composition according to <42> or <43>, wherein a content of the acid component in the rust inhibitor composition is preferably 0.5 mass % or more, more preferably 1 mass % or more, further preferably 2 mass % or more, and preferably 20 mass % or less, more preferably 15 mass % or less, further preferably 10 mass % or less.

45

The rust inhibitor composition according to any one of <42> to <44>, wherein the alkali component is an organic alkali.

46

The rust inhibitor composition according to any one of <42> to <45>, wherein a content of the alkali component in the rust inhibitor composition is preferably 0.5 mass % or more, more preferably 1 mass % or more, further preferably 2 mass % or more, and preferably 20 mass % or less, more preferably 15 mass % or less, further preferably 10 mass % or less.

47

The rust inhibitor composition according to any one of <36> to <46>, wherein pH of the rust inhibitor composition is preferably 3 or more, more preferably 5 or more, further preferably 7 or more, and preferably 12 or less, more preferably 10 or less, further preferably 9 or less.

48

The rust inhibitor composition according to any one of <36> to <47>, being a cutting oil, a rust preventive oil, or a detergent.

49

The rust inhibitor composition according to <48>, wherein when the rust inhibitor composition is used as a detergent, a temperature of the rust inhibitor composition is preferably 10° C. or higher, more preferably 30° C. or higher, further preferably 40° C. or higher, and preferably 90° C. or lower, more preferably 70° C. or lower, further preferably 60° C. or lower.

50

The rust inhibitor composition according to any one of <36> to <47>, being a coating formation material for forming a coating on a surface of a metal component.

51

The rust inhibitor composition according to <50>, wherein when the rust inhibitor composition is used as the coating formation material, the rust inhibitor composition contains water.

52

The rust inhibitor composition according to <51>, wherein a content of water in the rust inhibitor composition is preferably 80 mass % or more, more preferably 90 mass % or more, further preferably 95 mass % or more, and preferably 99.9 mass % or less, more preferably 99 mass % or less, further preferably 98 mass % or less.

53

A coating formation material comprising at least one kind of a compound represented by a Chemical Formula (1):

[Chemical Formula (1)]

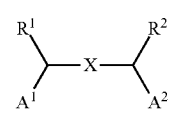

wherein $R^1$ is a hydrogen atom or an aliphatic hydrocarbon group having 1 or more and 33 or less carbon atoms, $R^2$ is an aliphatic hydrocarbon group having 1 or more and 33 or less carbon atoms, a total number of carbon atoms of $R^1$ and $R^2$ is 1 or more and 34 or less, X is a single bond or an aliphatic hydrocarbon group having 1 or more and 5 or less carbon atoms, and one of $A^1$ and $A^2$ is —OH and the other is —O—$CH_2$—CH(OH)—$CH_2$OH or —O—CH(—$CH_2$OH)$_2$.

54

A coating formation material comprising at least one kind of a compound represented by a Chemical Formula (1):

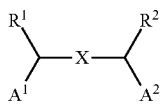

[Chemical Formula (1)]

wherein $R^1$ is a hydrogen atom or an aliphatic hydrocarbon group having 1 or more and 33 or less carbon atoms, $R^2$ is an aliphatic hydrocarbon group having 1 or more and 33 or less carbon atoms, X is a single bond or an aliphatic hydrocarbon group having 1 or more and 5 or less carbon atoms, a total number of carbon atoms of $R^1$, $R^2$ and X is 1 or more and 39 or less, and one of $A^1$ and $A^2$ is —OH and the other is —O—CH$_2$—CH(OH)—CH$_2$OH or —O—CH(—CH$_2$OH)$_2$.

55

The coating formation material according to <53> or <54>, being a rust inhibitor.

56

A coating obtained from the rust inhibitor according to any one of <1> to <35>, the rust inhibitor composition according to any one of <36> to <52>, or the coating formation material according to any one of <53> to <55>.

57

The coating according to <56>, wherein a thickness of the coating is preferably 1 nm or more, more preferably 3 nm or more.

58

A metal component comprising the coating according to <56> or <57>.

59

The metal component according to <58>, in which an iron member and a non-ferrous metal member are combined.

EXAMPLES

Hereinafter, a specific description is made of the present invention with reference to Examples. The content of each component is expressed in mass % unless otherwise indicated in Tables. Various measuring methods are as follows.

Method for Measuring Double Bond Distribution in Olefin

The double bond distribution in olefin was measured by gas chromatography (hereinafter, abbreviated as GC). Specifically, dimethyl disulfide was reacted with olefin to form a dithioated derivative, and then respective components were separated by GC. The double bond distribution in olefin was determined from respective peak areas. The apparatus used for measurement and analyzing conditions are as follows.

GC apparatus: Trade name HP6890 (manufactured by Hewlett-Packard Company)
Column: Trade name Ultra-Alloy-1 HT capillary column 30 m×250 μm×0.15 μm (manufactured by Frontier Laboratories, Ltd.)
Detector: Hydrogen flame ion detector (FID)
Injection temperature: 300° C.
Detector temperature: 350° C.
Oven: 60° C. (0 min.)→2° C./min.→225° C.→20° C./min.→350° C.→350° C. (5.2 min.)

Metal for Measuring Content Ratio of Structural Isomer

Measurement was performed by $^1$H-NMR for a mixture of 0.05 g of alkyl glyceryl ether, 0.2 g of trifluoroacetic anhydride, and 1 g of deuterated chloroform. Measuring conditions are as follows.

Nuclear magnetic resonance apparatus: Agilent 400-MR DD2, manufactured by Agilent Technologies, Inc.
Observation range: 6410.3 Hz
Data point: 65536
Measurement mode: Preset
Pulse width: 45°
Pulse delay time: 10 sec
Cumulative number: 120 times Production of Internal Olefin Production Example A1

Production of Internal Olefin Having 16 Carbon Atoms (Internal Olefin 1)

A flask equipped with a stirrer was charged with 7000 g (28.9 mol) of 1-hexadecanol (Product name; KALCOL 6098, manufactured by Kao Corporation) and 700 g (10 wt % with respect to the raw material alcohol) of γ-alumina (STREM Chemicals, Inc.) as a solid acid catalyst, followed by reaction at 280° C. for 32 hours under stirring with circulation of nitrogen (7000 mL/min) in the system. The alcohol conversion after completion of the reaction was 100%, and the purity of C16 olefin was 59.6%. The obtained crude C16 internal olefin was transferred to a distiller, followed by distillation at 136 to 160° C./4.0 mmHg to yield an internal olefin 1 having an olefin purity of 100%. The double bond distribution in the obtained internal olefin 1 was 0.2% at the C1 position, 15.8% at the C2 position, 14.5% at the C3 position, 15.7% at the C4 position, 17.3% at the C5 position, 16.5% at the C6 position, and 20.0% at the C7 position and the C8 position in total.

Production Example A2

Production of Internal Olefin Having 13 Carbon Atoms (Internal Olefin 2)

A reactor equipped with a stirrer was charged with 800 kg (3.0 kmol) of 1-octadecanol (Product name: KALCOL 8098, manufactured by Kao Corporation) and 80 kg (10 wt % with respect to the raw material alcohol) of activated alumina GP-20 (Mizusawa Industrial Chemicals, Ltd.) as a solid acid catalyst, followed by reaction at 280° C. for 16 hours under stirring with circulation of nitrogen (15 L/min) in the system. The alcohol conversion after completion of the reaction was 100%, and the purity of C18 olefin was 93.7%. The obtained crude C18 internal olefin was transferred to a distiller, followed by distillation at 163 to 190° C./4.6 mmHg to yield an internal olefin 2 having an olefin purity of 100%. The double bond distribution in the obtained internal olefin 2 was 0.3% at the C1 position, 13.3% at the C2 position, 12.6% at the C3 position, 13.9% at the C4 position, 14.8% at the C5 position, 13.7% at the C6 position, 12.6% at the C7 position, and 18.8% at the C8 position and the C9 position in total.

Production Example A3

Production of Internal Olefin Having 14 Carbon Atoms (Internal Olefin 3)

An internal olefin 3 was obtained in the same manner as in Production Example A1 except that 23.3 mol of 1-tetradecanol (Product name: KALCOL 4038, manufactured by Kao Corporation) was used in place of 23.9 mol of 1-hexadecanol (Product name: KALCOL 6038, manufactured by Kao Corporation) for Production Example A1. The double bond distribution in the obtained internal olefin 3 was 1.3% at the C1 position, 31.3% at the C2 position, 23.8% at the C3 position, 21.0% at the C4 position, 8.5% at the C5 position, and 13.6% at the C6 position and C7 position in total.

Production of Internal Epoxide

Production Example B1

Production of Internal Epoxide Having 16 Carbon Atoms (Internal Epoxide 1)

A flask equipped with a stirrer was charged with the internal olefin 1 (800 g, 3.56 mol) obtained in Production Example A1, 107 g (1.78 mol) of acetic acid (manufactured by Wako Pure Chemical Industries, Ltd.), 15.6 g (0.15 mol) of sulfuric acid (manufactured by Wako Pure Chemical Industries, Ltd.), 415.7 g (4.28 mol) of 35% hydrogen peroxide (manufactured by Wako Pure Chemical Industries, Ltd.), and 25.3 g (0.18 mol) of sodium sulfate (manufactured by Wako Pure Chemical Industries, Ltd.), followed by reaction at 50° C. for 4 hours. Thereafter, the temperature was raised to 70° C. to allow the mixture to react further for 2 hours. After the reaction, the layers were separated to remove an aqueous layer, and an oil layer was washed with ion-exchanged water, a saturated aqueous sodium carbonate solution (manufactured by Wako Pure Chemical Industries, Ltd.), a saturated aqueous sodium sulfite solution (manufactured by Wako Pure Chemical Industries, Ltd.), and 1% saline (manufactured by Wako Pure Chemical Industries, Ltd.), followed by concentration in an evaporator to yield 820 g of an internal epoxide 1.

Production Example B2

Production of Internal Epoxide Having 13 Carbon Atoms (Internal Epoxide 2)

A flask equipped with a stirrer was charged with the internal olefin 2 (595 g, 2.36 mol) obtained in Production Example A2, 71.7 g (1.20 mol) of acetic acid (manufactured by Wako Pure Chemical Industries, Ltd.), 9.8 g (0.10 mol) of sulfuric acid (manufactured by Wako Pure Chemical Industries, Ltd.), and 324 g (4.00 mol) of 35% hydrogen peroxide (manufactured by Wako Pure Chemical Industries, Ltd.), followed by reaction at 50° C. for 4 hours. Thereafter, the temperature was raised to 80° C. to allow the mixture to react further for 5 hours. After the reaction, the layers were separated to remove an aqueous layer, and an oil layer was washed with ion-exchanged water, a saturated aqueous sodium carbonate solution (manufactured by Wako Pure Chemical Industries, Ltd.), a saturated aqueous sodium sulfite solution (manufactured by Wako Pure Chemical Industries, Ltd.), and ion-exchanged water, followed by concentration in an evaporator to yield 629 g of an internal epoxide 2.

Production Example B3

Production of Internal Epoxide Having 14 Carbon Atoms (Internal Epoxide 3)

An internal epoxide 3 was obtained in the same manner as in Production Example B1 except that the internal olefin 3 (3.56 mol) obtained in Production Example A3 was used in place of the internal olefin 1 (3.36 mol) obtained in Production Example A1.

Production of Reactant of Epoxide and Glycerin (alkyl glyceryl ether, AGE)

Hereinafter, the alkyl glyceryl ether is referred to as AGE. In addition, AGE1, AGE2, AGE3, and the like represent alkyl glyceryl ether 1, alkyl glyceryl ether 2, alkyl glyceryl ether 3, and the like, respectively.

Production Example C1

Production of Reactant of Internal Epoxide 1 and Glycerin (AGE1)

A flask equipped with a stirrer was charged with 2298 g (25.0 mol) of glycerin (manufactured by Wako Pare Chemical Industries, Ltd.) and 0.122 g (1.25 mmol) of 98% sulfuric acid (manufactured by Wako Pure Chemical Industries, Ltd.), and the temperature was raised to 130° C. Thereafter, the internal epoxide 1 (300 g, 1.25 mol) obtained in Production example B1 was added dropwise over 1 hour, followed by reaction at 130° C./8 hours. Hexane was added to the liquid obtained by this reaction, followed by washing with ion-exchanged water. Subsequently, concentration was performed under reduced pressure in an evaporator to yield 400 g of AGE1. The obtained AGE1 wherein in the Chemical Formula (1), $R^1$ and $R^2$ each contain an alkyl group having 1 to 13 carbon atoms, the total number of carbon atoms of $R^1$ and $R^2$ is 14, X is a single bond, one of $A^1$ and $A^2$ is —OH and the other is —O—CH$_2$—CH(OH)—CH$_2$OH or —O—CH(—CH$_2$—OH)$_2$, contained 73% ether alcohol 1 (AGE obtained by reacting the hydroxyl group at the 1-position of glycerin with the epoxy group) in which $A^1$ or $A^2$ was —O—CH$_2$—CH(OH)—CH$_2$OH, and 27% ether alcohol 2 (AGE obtained by reacting the hydroxyl group at the 2-position of glycerin with the epoxy group) in which $A^1$ or $A^2$ was —O—CH(—CH$_2$—OH)$_2$.

Production Example C2

Production of Reactant of Internal Epoxide 2 and Glycerin (AGE2)

An AGE2 was obtained in the same manner as in Production Example C1 except that the internal epoxide 2 (1.25 mol) obtained in Production Example B2 was used in place of the internal epoxide 1 (1.25 mol) obtained in Production Example B1. The obtained AGE2 wherein in the Chemical Formula (1), $R^1$ and $R^2$ each contain an alkyl group having 1 to 15 carbon atoms, the total number of carbon atoms of $R^1$ and $R^2$ is 16, X is a single bond, one of $A^1$ and $A^2$ is —OH and the other is —O—$CH_2$—CH(OH)—$CH_2$OH or —O—CH(—$CH_2$—OH)$_2$, contained 72% AGE obtained by reacting the hydroxyl group at the 1-position of glycerin with the epoxy group, and 28% AGE obtained by reacting the hydroxyl group at the 2-position of glycerin with the epoxy group.

Production Example C3

Production of Reactant of Internal Epoxide 3 and Glycerin (AGE3)

An AGE3 was obtained in the same manner as in Production Example C1 except that the internal epoxide 3 (1.25 mol) obtained in Production Example B3 was used in place ox the internal epoxide 1 (1.25 mol) obtained in Production Example B1. The obtained AGE3 wherein in the Chemical Formula (1), $R^1$ and $R^2$ each contain an alkyl group having 1 to 11 carbon atoms, the total number of carbon atoms of $R^1$ and $R^2$ is 12, X is a single bond, one of $A^1$ and $A^2$ is —OH and the other is —O—$CH_2$—CH(OH)—$CH_2$OH or —O—CH(—$CH_2$—OH)$_2$, contained 74% AGE obtained by reacting the hydroxyl group at the 1-position of glycerin with the epoxy group, and 26% AGE obtained by reacting the hydroxyl group at the 2-position of glycerin with the epoxy group.

Production Example C4

Production of Reactant of C16 Terminal Epoxide and Glycerin (AGE4)

An AGE4 was obtained in the same manner as in Production Example C1 except that 1.25 mol of a C16 terminal epoxide (manufactured by Tokyo Chemical Industry Co., Ltd.) was used in place of the internal epoxide 1 (1.25 mol) obtained in Production Example B1. The obtained AGE4 wherein in the Chemical Formula (1), $R^1$ is a hydrogen atom, $R^2$ is an aliphatic hydrocarbon group having 14 carbon atoms, X is a single bond, one of $A^1$ and $A^2$ is —OH and the other is —O—$CH_2$—CH(OH)—$CH_2$OH or —O—CH(—$CH_2$—OH)$_2$, contained 50% AGS obtained by reacting the hydroxyl group at the 1-position of glycerin with the epoxy group, and 50% AGE obtained by reacting the hydroxyl group at the 2-position of glycerin with the epoxy group.

Production Example C5

Production of Reactant of C18 Terminal Epoxide and Glycerin (AGE5)

An AGE5 was obtained in the same manner as in Production Example C1 except that 1.25 mol of a C18 terminal epoxide (manufactured by Tokyo Chemical Industry Co., Ltd.) was used in place of the internal epoxide 1 (1.25 mol) obtained in Production Example B1. The obtained AGE5 wherein in the Chemical Formula (1), $R^1$ is a hydrogen atom, $R^2$ is an aliphatic hydrocarbon group having 16 carbon atoms, X is a single bond, one of $A^1$ and $A^2$ is —OH and the other is —O—$CH_2$—CH(OH)—$CH_2$OH or —O—CH(—$CH_2$—OH)$_2$, contained 51% AGE obtained by reacting the hydroxyl group at the 1-position of glycerin with the epoxy group, and 49% AGE obtained by reacting the hydroxyl group at the 2-position of glycerin with the epoxy group.

Examples 1-1 to 1-13, Comparative Examples 1-1 to 1-4

The components shown in Table 1 were mixed at the blending ratios shown in Table 1 to prepare rust inhibitor compositions. Using each prepared rust inhibitor composition, a water resistance test was performed by the following method. The results are shown in Table 1. In Table 1, AGE is an alkyl glyceryl ether, BDG is diethylene glycol monobutyl ether (solubilizing agent) and TEA is triethanolamine (alkali component).

Water Resistance Test (Aluminum)

In a 100 mL glass beaker, 100 g of the rust inhibitor composition was added, followed by heating to 50° C. In the rust inhibitor composition, an aluminum alloy plate (ADC12, 50 mm×20 mm×1.6 mm) degreased and washed with acetone was immersed for 30 seconds. Thereafter, the aluminum alloy plate was taken out and dried by air-blowing. Next, the aluminum alloy plate was immersed in 50 g of water heated to 50° C. for 1 hour. Thereafter, the amount of aluminum ions eluted in the water was measured using an ICP emission spectrophotometer (Agilent 5110 ICP-OES manufactured by Agilent), and the amount of aluminum eluted per unit area ($g/m^2$) was calculated from the measurement result and the surface area of the aluminum alloy plate. In addition, the surface of the aluminum alloy plate after the test was visually observed and evaluated according to the following criteria.

1: No corrosion is observed

2: Only partial corrosion is observed

3: Entire surface corrosion is observed

Water Resistance Test (Iron)

In a 100 mL glass beaker, 100 g of the rust inhibitor composition was added, followed by heating to 60° C. In the rust inhibitor composition, a steel plate (SPCC, 50 mm×20 mm×0.8 mm) degreased and washed with acetone was immersed for 30 seconds. Thereafter, the steel plate was taken out and dried by air-blowing. Next, the steel plate was immersed in 50 g of water heated to 50° C. for 1 hour. Thereafter, the amount of iron ions eluted in the water was measured using an ICP emission spectrophotometer (Agilent 5.110 ICP-OES manufactured by Agilent), and the amount of iron eluted per unit area ($g/m^2$) was calculated from the measurement result and the surface area of the steel plate. In addition, the surface of the steel plate after the test was visually observed and evaluated according to the following criteria.

1: No rust is observed

2: Only point rust is observed

3: Entire surface rust is observed

TABLE 1

| | Rust Inhibitor Composition | | | | | | Evaluation | | | | |
|---|---|---|---|---|---|---|---|---|---|---|---|
| | Rust Inhibitor | BDG | Caprylic Acid | TEA | Water | Total Amount | Appearance of Aqueous Solution | Amount of Al Eluted from Al Alloy g/m² | Amount of Fe Eluted from Steel Plate g/m² | Appearance of Test Piece | |
| | Kind | Mass % | Mass % | Mass % | Mass % | Mass % | Mass % | | | | Al Alloy | Steel Plate |
| Example 1-1 | AGE2 | 0.1 | — | — | — | Balance | 100 | Turbidity | 0.1 | 1.3 | 1 | 1 |
| Example 1-2 | AGE2 | 1 | — | — | — | Balance | 100 | Turbidity | 0.1 | 1.2 | 1 | 1 |
| Example 1-3 | AGE1 | 0.1 | — | — | — | Balance | 100 | Turbidity | 0.1 | 4.3 | 1 | 2 |
| Example 1-4 | AGE1 | 1 | — | — | — | Balance | 100 | Turbidity | 0.1 | 1.2 | 1 | 1 |
| Example 1-5 | AGE3 | 1 | — | — | — | Balance | 100 | Turbidity | 0.1 | 1.7 | 1 | I |
| Example 1-6 | AGE2 | 1 | 15 | — | — | Balance | 100 | Transparent | 0.1 | 1.1 | 1 | 1 |
| Example 1-7 | AGE1 | 1 | 15 | — | — | Balance | 100 | Transparent | 0.1 | 1.5 | 1 | 1 |
| Example 1-8 | AGE2 | 1 | — | 4 | 6 | Balance | 100 | Transparent | 0.1 | 1.3 | I | |
| Example 1-9 | AGE1 | 1 | — | 4 | 6 | Balance | 100 | Transparent | 0.1 | 1.1 | 1 | 1 |
| Example 1-10 | AGE5 | 1 | 10 | — | — | Balance | 100 | Turbidity | 0.1 | 1.5 | 1 | 1 |
| Example 1-11 | AGE4 | 1 | 10 | — | — | Balance | 100 | Turbidity | 0.8 | 3.6 | 2 | 2 |
| Example 1-12 | AGE2 | 100 | — | — | — | — | 100 | Transparent | 0.1 | 1.2 | 1 | 1 |
| Example 1-13 | AGE1 | 100 | — | — | — | — | 100 | Transparent | 0.1 | 1.2 | 1 | 1 |
| Comparative Example 1-1 | — | — | — | — | — | Balance | 100 | Transparent | 2.2 | 31 | 3 | 3 |
| Comparative Example 1-2 | — | — | 15 | — | — | Balance | 100 | Transparent | 2.5 | 8.2 | 3 | 3 |
| Comparative Example 1-3 | — | — | 10 | — | — | Balance | 100 | Transparent | 2.2 | 10.4 | 3 | 3 |
| Comparative Example 1-4 | — | — | — | 4 | 6 | Balance | 100 | Transparent | 2.7 | 28 | 3 | 3 |

Example 2

Table 2 shows blending examples of the rust inhibitor composition. In Table 2, AGE is an alkyl glyceryl ether, BDG is diethylene glycol monobutyl ether (solubilising agent) and TEA is triethanol amine (alkali component).

TABLE 2

| | Rust Inhibitor Composition | | | | | | Evaluation |
|---|---|---|---|---|---|---|---|
| | Rust Inhibitor | BDG | Caprylic Acid | TEA | Water | Total Amount | Appearance of Aqueous Solution |
| | Kind | Mass % | Mass % | Mass % | Mass % | Mass % | Mass % | |
| Blending Example 1 | AGE2 | 5 | 75 | — | — | Balance | 100 | Transparent |
| Blending Example 2 | AGE1 | 5 | 75 | — | — | Balance | 100 | Transparent |
| Blending Example 3 | AGE2 | 8 | — | 32 | 46 | Balance | 100 | Transparent |
| Blending Example 4 | AGE1 | 8 | — | 32 | 48 | Balance | 100 | Transparent |

Example 3

Rust Inhibitor Treatment of Steel Plate (Fa Substrate)

As an Fe substrate before the rust inhibitor treatment, a steel plate (SPCC, 50 mm×20 mm×0.8 mm, hereinafter referred to as Fe substrate) degreased and washed with acetone was used. In a 100 mL glass beaker, 100 g of the rust inhibitor composition prepared in Example 1-2 was added, followed by heating to 60° C. In the rust inhibitor composition, the Fe substrate before the rust inhibitor treatment was immersed for 30 seconds. Thereafter, the Fe substrate was taken out, dried by air-blowing to prepare an Fe substrate after rust inhibitor treatment.

Rust Inhibitor Treatment of Aluminum Alloy Plate (Al Substrate)

As an Al substrate before the rust inhibitor treatment, an aluminum alloy plate (ADC 12, 50 mm×20 mm×1.6 mm, hereinafter referred to as Al substrate) degreased and washed with acetone was used. In a 100 mL glass beaker, 100 g of the rust, inhibitor composition prepared in Example 1-2 was added, followed by heating to 5.0° C. In the rust inhibitor composition, the Al substrate before the rust inhibitor treatment was immersed for 30 seconds. Thereafter, the Al substrate was taken out, dried by air-blowing to prepare an Al substrate after mast, inhibitor treatment.

The Fe substrate and the Al substrate before and after the rust inhibitor treatment were subjected to element mapping using the following method. Element mapping of Fe and C was performed for the Fe substrate, and element mapping of Al and C was performed for the Al substrate. The results are shown in the FIGURE. Each of the substrates was displayed in white when the element was present, and in black when the element was not present.

Element Mapping

The element, mapping of the substrate surface was performed using a tabletop microscope Miniscope (registered trademark) TM3000 (manufactured by Hitachi High-Tech Corporation) and an energy dispersive X-ray analyzer Swift ED3000 (manufactured by Hitachi High-Tech Corporation). The measurement conditions are as follows: acceleration voltage; 5.0 kV, resolution: 128×104 pixels, display resolution: 100%, and process time: 5.

The FIGURE shows that a coating of the compound represented by the Chemical Formula (1) is uniformly formed on the Fe substrate surface and the Al substrate surface.

INDUSTRIAL APPLICABILITY

The rust inhibitor, the rust inhibitor composition, and the coating formation material of the present invention are useful as a forming material for a rust preventive coating with which the surface of various metal components is coated. The rust inhibitor composition of the present invention is useful as a cutting oil, a rust preventive oil, or a detergent.

The invention claimed is:

1. A rust inhibitor comprising at least one kind of a compound represented by a Chemical Formula (1):

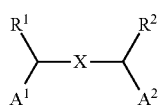

[Chemical Formula (1)]

wherein $R^1$ is a hydrogen atom or an aliphatic hydrocarbon group having 1 or more and 33 or less carbon atoms, $R^2$ is an aliphatic hydrocarbon group having 1 or more and 33 or less carbon atoms, a total number of carbon atoms of $R^1$ and $R^2$ is 1 or more and 34 or less, X is a single bond or an aliphatic hydrocarbon group having 1 or more and 5 or less carbon atoms, and one of $A^1$ and $A^2$ is —OH and the other is —O—$CH_2$—CH(OH)—$CH_2OH$ or —O—CH(—$CH_2$—OH)$_2$.

2. The rust inhibitor according to claim 1, wherein in the compound represented by the Chemical Formula (1), X is a single bond.

3. The rust inhibitor according to claim 2, wherein in the compound represented by the Chemical Formula (1), $R^1$ is an aliphatic hydrocarbon group having 1 or more and 33 or less carbon atoms.

4. The rust inhibitor according to claim 2, comprising a compound 1 in which in the Chemical Formula (1), one of $A^1$ and $A^2$ is —OH and the other is —O—$CH_2$—CH(OH)—$CH_2OH$, and a compound 2 in which in the Chemical Formula (1), one of $A^1$ and $A^2$ is —OH and the other is —O—CH(—$CH_2$—OH)$_2$.

5. A rust inhibitor composition comprising the rust inhibitor according to claim 2.

6. The rust inhibitor according to claim 1, wherein in the compound represented by the Chemical Formula (1), $R^1$ is an aliphatic hydrocarbon group having 1 or more and 33 or less carbon atoms.

7. The rust inhibitor according to claim 6, comprising a compound 1 in which in the Chemical Formula (1), one of $A^1$ and $A^2$ is —OH and the other is —O—$CH_2$—CH(OH)—$CH_2OH$, and a compound 2 in which in the Chemical Formula (1), one of $A^1$ and $A^2$ is —OH and the other is —O—CH(—$CH_2$—OH)$_2$.

8. A rust inhibitor composition comprising the rust inhibitor according to claim 6.

9. The rust inhibitor according to claim 1, comprising a compound 1 in which in the Chemical Formula (1), one of $A^1$ and $A^2$ is —OH and the other is —O—$CH_2$—CH(OH)—$CH_2OH$, and a compound 2 in which in the Chemical Formula (1), one of $A^1$ and $A^2$ is —OH and the other is —O—CH(—$CH_2$—OH)$_2$.

10. A rust inhibitor composition comprising the rust inhibitor according to claim 9.

11. A rust inhibitor composition comprising the rust inhibitor according to claim 1.

12. The rust inhibitor composition according to claim 11, further comprising a solubilizing agent.

13. The rust inhibitor composition according to claim 11, wherein the rust inhibitor composition is a cutting oil, a rust preventive oil, or a detergent, and comprises the compound represented by the Chemical Formula (1).

14. A coating obtained from the rust inhibitor composition according to claim 11.

15. A metal component comprising the coating according to claim 14.

16. A coating obtained from the rust inhibitor according to claim 1.

17. A metal component comprising the coating according to claim 16.

18. A coating formation material comprising at least one kind of a compound represented by a Chemical Formula (1):

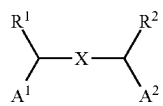

[Chemical Formula (1)]

wherein $R^1$ is a hydrogen atom or an aliphatic hydrocarbon group having 1 or more and 33 or less carbon atoms, $R^2$ is an aliphatic hydrocarbon group having 1 or more and 33 or less carbon atoms, a total number of carbon atoms of $R^1$ and $R^2$ is 1 or more and 34 or less, X is a single bond or an aliphatic hydrocarbon group having 1 or more and 5 or less carbon atoms, and one of $A^1$ and $A^2$ is —OH and the other is —O—$CH_2$—CH(OH)—$CH_2OH$ or —O—CH(—$CH_2$—OH)$_2$.

19. A coating obtained from the coating formation material according to claim 18.

20. A metal component comprising the coating according to claim 18.

* * * * *